United States Patent
Anselmi et al.

(10) Patent No.: US 11,273,107 B2
(45) Date of Patent: Mar. 15, 2022

(54) EYE MAKE-UP COMPOSITIONS COMPRISING GRAPHENE

(71) Applicant: PRODOTTI GIANNI S.R.L., Milan (IT)

(72) Inventors: Cecilia Anselmi, Siena (IT); Marisanna Centini, San Quirico d'Orcia (IT); Giulia Signori, Colle di Val d'Elsa (IT); Maria Francesca Tola, Partinico (IT)

(73) Assignee: PRODOTT GIANNI S.R.L, Milan (IT)

( * ) Notice: Subject to any disclaimer, the term of this patent is extended or adjusted under 35 U.S.C. 154(b) by 0 days.

(21) Appl. No.: 16/769,057

(22) PCT Filed: Dec. 3, 2018

(86) PCT No.: PCT/EP2018/083259
§ 371 (c)(1),
(2) Date: Jun. 2, 2020

(87) PCT Pub. No.: WO2019/110460
PCT Pub. Date: Jun. 13, 2019

(65) Prior Publication Data
US 2020/0330344 A1    Oct. 22, 2020

(30) Foreign Application Priority Data

Dec. 5, 2017  (IT) .................. 102017000140453

(51) Int. Cl.
| | | |
|---|---|---|
| *A61K 8/25* | (2006.01) | |
| *A61K 8/92* | (2006.01) | |
| *A61K 8/37* | (2006.01) | |
| *A61Q 1/10* | (2006.01) | |

(52) U.S. Cl.
CPC .............. *A61K 8/25* (2013.01); *A61K 8/37* (2013.01); *A61K 8/922* (2013.01); *A61Q 1/10* (2013.01); *A61K 2800/30* (2013.01); *A61K 2800/412* (2013.01); *A61K 2800/413* (2013.01); *A61K 2800/43* (2013.01)

(58) Field of Classification Search
CPC ... A61K 8/25; A61K 8/92; A61K 8/37; A61Q 1/10
See application file for complete search history.

(56) References Cited

U.S. PATENT DOCUMENTS

2020/0360429 A1* 11/2020 Kang .................... A23K 20/20

FOREIGN PATENT DOCUMENTS

| FR | 2 848 423 A1 | 6/2004 |
|---|---|---|
| WO | WO 2008/140872 A1 | 11/2008 |

* cited by examiner

*Primary Examiner* — Zohreh A Fay
(74) *Attorney, Agent, or Firm* — Polsinelli PC

(57) ABSTRACT

New natural-based, eye make-up cosmetic composition, comprising graphene, being free from synthetic polymers, provided with optimal features for ease of distribution and high-definition.

15 Claims, 3 Drawing Sheets

A

C

B

D

EYE MAKE-UP COMPOSITIONS COMPRISING GRAPHENE

CROSS REFERENCE TO RELATED APPLICATIONS

This application is a National Phase filing under 35 U.S.C. § 371 of PCT/EP2018/083259 filed on 3 Dec. 2018; which application in turn claims priority to Application No. 102017000140453 filed in France on 5 Dec. 2017. The entire contents of each application are hereby incorporated by reference.

TECHNICAL FIELD

The present invention relates to the field of research and development of innovative natural-based, organic and ecologically sustainable cosmetic products that are highly performing and safe. In particular, new eye make-up compositions are described, comprising graphene, and associated with emulsifiers and other ingredients known in the sector.

BACKGROUND ART

Eye make-up products comprise different types of products, such as mascara for eyelashes and eyebrows, and eyeliner, which defines the eye contour.

Mascara has to respect particular cosmetic effects, for example, the volume building (volumizing feature), lengthening and curling of eyelashes, the definition, volume and thickening effect of eyebrows; further, mascara has to present features that are useful for its applicability, that is, enough smoothness, evenly distribution, adherence to eyelashes, absence of clumps, easy removal when removing make-up, etc.; such features are not always easy to reconcile with the cosmetic effects just mentioned.

Mascaras are generally based on emulsifying systems associated with oils, waxes or lipophilic substances, in order to obtain a sufficiently fluid base; polymeric and/or fibrous products are associated with them that are useful to confer consistence and obtain the thickening/lengthening of eyelashes and the definition of eyebrows, as well as dyes to confer color; the use of film coating agents is also widely spread, which favor the adherence of the product and the uniform coverage of eyelashes and eyebrows.

With regard to eyeliners, they have to respond to other particular needs of the client, such as the high definition of the stroke, the easiness to distribute the product both on the upper and lower eyelid. Further, being a product that is applied externally near the eye, which can be subject to lacrimation, it is very important that the eyeliner is a high-endurance one (the so-called "long-lasting" effect), that is, it must not release color over time if it comes into contact with water or in the presence of moisture, thus causing smudging around the eye.

In this cosmetic sector, the use of synthetic film coating polymers such as polyacrylates, polyurethanes, polyamides, polyolefins, silicones and the polymers thereof, polyesters, polyacetates, etc., is very common; such products are increasingly less desired by consumers, both because of the possibility of incorporating toxic residues deriving from the synthesis process and because of the increasing trend to prefer natural-based products with a low impact on the organism and on the environment.

However, the use of these products is difficult to avoid since they result essential to favor a high adherence and a homogeneous coverage of the eyelashes and the eyebrows, so that the trend to reduce the "synthetic" component of mascara is often accompanied by a reduced performance, for example, in terms of adherence or evenness of coverage.

The present invention faces and solves these problems, making a new composition available that is for eye make-up "on a natural basis", simple and efficient, and that avoids the use of synthetic polymers, having performing features that are equal to or even higher than those of commonly used products.

DISCLOSURE OF INVENTION

The object of the present invention is a new eye make-up composition, which can be a mascara (suitable for the application on eyelashes or eyebrows) or an eyeliner, comprising graphene.

The composition does not require the use of synthetic polymers and synthetic fibers, and is provided with optimal features for volumizing, lengthening of the eyelashes and adherence thereto, for definition and filling of the eyebrows, and for high-endurance on the eye contour when applied on the skin.

MODES FOR CARRYING OUT THE INVENTION

Figure 1:
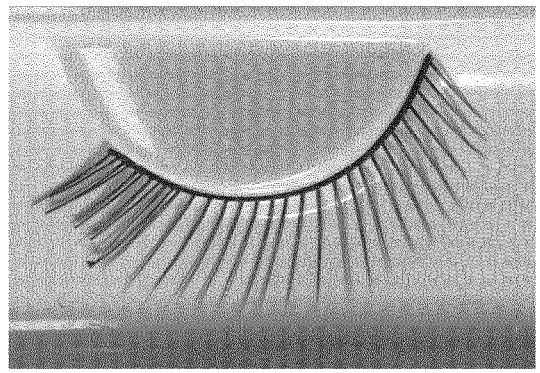
FIG. 1: artificial eyelashes (control) used for the assessment of the effects of the compositions of the invention and of the commercial reference.

The main object of the invention is a natural-based, make-up cosmetic composition comprising graphene, free from synthetic polymers.

The term "natural-based" identifies a mascara in which the use of natural substances is preferred, in particular thanks to the exclusive use of vegetal fibers and avoiding the use of synthetic polymers; concerning the other ingredients, the term "natural-based" indicates the main use of natural substances, but does not exclude the use, in minor quantities, of non-natural substances, such as synthesis or semi-synthesis substances.

The composition of the present invention can be a mascara, suitable for the application on eyelashes and eyebrows, or an eyeliner.

In the present text by "mascara" is intended, as commonly known in the sector, a product suitable for the application on eyelashes and eyebrows, and for the temporary covering of the same, comprising characteristic ingredients of mascaras such as emulsifiers, fibers, oils, waxes, dyes.

By the term "eyeliner" as used herein is intended, as commonly known in the sector, a product suitable for the application on the upper and/or lower eyelid, for defining the eye contour, comprising characteristic ingredients of eyeliners such as emulsifiers, dyes, wetting solutions, alcohol and film coating agents.

The term "synthetic polymers" as used herein refers to synthesis polymers, typically used as film coating agents in the known compositions and are represented, without limitation, by: acrylic polymers or copolymers (for example, acrylates, methacrylates, alkyl acrylates, alkyl methacrylates, polyacrylates, polymethacrylates), polyolefins, polyvinyls, polyurethanes, polyamides, polyimides, polyethers, polyesters, fluoropolymers, polyethers, polyacetates, polycarbonates, epoxides, aldehyde resines, polysiloxanes, polyquaterniums and the like. Such polymers, as mentioned above, are absent or substantially absent in the present compositions.

As mentioned above, in the cosmetic composition object of the invention, graphene is present.

Such ingredient is known in the state of the art in the preparation of facial masks or rub-on compositions.

For instance, international patent application WO 2016199997 describes a cosmetic composition to be applied on the skin containing quantum dots of graphene, whose function is that of protecting from UV.

CN 106038324 describes a composition for a heating facial mask comprising a graphene film, where the resistivity of such film is deployed.

CN 106821852 describes an emulsion containing quantum dots of graphene, whose function is that of absorbing the dirt of the skin surface, hydrate and adjust the water-oil skin balance, cleanse the skin and inhibit the growth of pathogens.

CN 106821776 describes a liquid composition containing graphene for the treatment of acne.

The Applicant has instead developed now a composition suitable for eye make-up, comprising graphene.

Particularly, the graphene used in the present invention is produced from natural graphite and obtained by physical expansion; consequently, it is a product free from harmful chemical substances.

The graphene used in the present composition is generally comprised between 5 and 15% by weight on the weight of the final composition, preferably 10%. The particles of said graphene can have, for example, a length comprised between 5 and 10 µm and a thickness comprised between 0.5 and 5 nm. Preferably, graphene is used in form of paste, for example, like commercially available by the company DIRECTA PLUS under the name "Graphene Paste G+".

It can be used as it is or in form of said water-based concentrated paste or in any other form compatible with mascara/eyeliner formulations.

According to an embodiment wherein the composition is a mascara, the composition further comprises waxes in a weight percentage comprised between 2 and 20% on the weight of the composition.

Graphene, in the presence of waxes, interposes in their molecular structures, thus originating an improved volumizing and curling effect of the eyelashes.

In addition to graphene, and eventually to the mentioned waxes, the present composition contains ingredients that are commonly requested in the eye make-up sector, such as mascara and eyeliner.

With illustrating but not limiting purposes, we can mention the following classes: emulsifiers, oils, dyes, preservatives, antioxidants generally in a watery vehicle; film coating agents (constituted by synthetic polymers) are not necessary, being such function efficiently accomplished by the presence of graphene; the composition can therefore be exempt from such film coating agents.

Emulsifiers are generally used in a weight percentage comprised between 1 and 10% on the weight of the mascara, and can be widely chosen among the commercially available ones. Not limiting examples are: potassium cetyl phosphate, glyceryl stearate citrate or glyceryl oleate citrate; other possible emulsifiers are those comprising starches, gums and/or fibers.

Oils are generally used in a weight percentage comprised between 2 and 20% on the weight of the mascara, and can be widely chosen among the commercially available ones; examples of oils are: triglycerides of caprylic/capric acid, tricaprylin, isoamyl laurate, vegetal oils, such as castor oil, sesame, linen, coconut, corn, cotton seeds, olive, palm, illipe, rape, soy, sunflower, walnut, avocado, camellia, macadamia walnut, grapes seeds, peanut, jojoba oils, etc.

In a preferred embodiment wherein the present composition is a mascara for the application to the eyelashes, castor oil is present in a weight percentage comprised between 1.5%-3.5% with respect to the weight of the mascara, while isoamyl laurate is present in a weight percentage comprised between 2.0%-3.0% with respect to the weight of the mascara.

In the embodiment wherein such composition is a mascara for the application to the eyebrows, castor oil is present in a weight percentage comprised between 0.3%-0.7% with respect to the weight of the mascara, while isoamyl laurate is present in a weight percentage comprised between 3.0%-4.0% with respect to the weight of the mascara.

Thanks to these different proportions of said oils, an optimized product is obtained for the application to the eyelashes or the eyebrows.

Specifically, the mascara composition as defined above for the application to the eyebrows shows ease of application and a surprisingly volumizing effect, due, among other things, to the efficient adherence of graphene to the eyebrows and to the presence of waxes and of isoamyl laurate: the latter, being volatile, leaves on the eyebrows a drier and more enduring product. Said proportions can be varied on the basis of the physicochemical properties of the oil used.

Waxes are generally used in a weight percentage comprised between 2 and 20% on the weight of the mascara, and can be widely chosen among those available in commerce. Non-limiting examples are: beeswax, spermaceti, lanolin, shellac, carnauba wax, candelilla wax, sugar cane wax, rice wax, olive wax. Among the preferred ones are to be mentioned carnauba wax and beeswax.

Dyes can be chosen as preferred among pigments, being mineral or organic. Pigments can be white or colored, eventually pearly. Among the mineral pigments titanium dioxide, coated titanium dioxide, iron, chrome oxides, manganese violet, ultramarine, etc. Among the organic pigments carbon black and those allowed by regulation (CE) 1223/2009 for the ocular area.

An example of black dye is the mixture C.I. 77266, Ceteareth-25, sodium carbonate, sorbitol, citric acid. Examples of white pearly pigments are mica coated with titanium dioxide or bismuth oxychloride. An example of colored pigment is mica with titanium dioxide, iron oxides, etc. Dyes are generally used in a weight percentage comprised between 1 and 20% on the weight of the mascara.

Preservatives and antioxidants, according to the invention, can be chosen among those available and accepted in products with "natural" connotations, generally used in a weight percentage variable according to known quantities on the basis of the specific preservative. Non-limiting examples of preservatives and antioxidants are benzoic acid, sorbic acid, dehydroacetic acid, benzyl alcohol, anisic acid, tocopherol and derivates, tocopherol-based mixtures, etc.

Further possible ingredients are, by way of non-limiting example: consistency factors, in proportions preferably comprised between 1 and 10% by weight on the mascara (e.g. glyceryl behenate, glyceryl stearate), additives with "caring" effect, perfumes, emollients, sequestrants, neutralizing agents, sun filters, sprays, fillers, rheology modifiers, stabilizers, pH correctors, moisteners (e.g. glycerin), moisturizers, vitamins, hyaluronic acid, etc. In particular, in the present compositions, amounts of glycerin up to 20%, preferably between 5% and 15% by weight on the weight of the composition were found particularly effective. Thus, according to a preferred embodiment, the present natural-based, make-up cosmetic compositions, free from synthetic polymers, comprise 5-10% graphene and up to 20% (e.g. 5-15%) glycerin, all these amounts being meant by weight on the weight of the composition; among them, particularly preferred are the compositions comprising 5-10% graphene, up to 20% (e.g. 5-15% glycerin), 2-20% oils and 1-10% emulsifiers, all these amounts being meant by weight on the weight of the composition; among them particularly preferred are compositions specific for mascara, comprising 5-10% graphene, up to 20% (e.g. 5-15% glycerin), 2-20% waxes, 2-20% oils and 1-10% emulsifiers, all these amounts being meant by weight on the weight of the composition.

Further to the mentioned ingredients, the composition of the invention, used as an eyeliner, comprises gelling agents and skin lenitive compounds.

The carrier is a watery solvent, preferably water, typically in emulsified phase, preferably oil-in-water, with the above mentioned components.

An important feature of the composition of the present invention is the absence or substantial absence of any polymer of synthetic nature (such ingredients are widely used in mascaras, particularly as film coating agents); in fact graphene, in combination with the above mentioned components, confers to the products (that is, mascara and eyeliner) optimal adherence and coverage evenness features so as to render the use of such agents superfluous; advantageously, the absence of synthesis polymers increases the pleasantness of the product and, above all, avoids to expose the user to traces of by-products deriving from the processes of polymerization; it is thus obtained a "safer" cosmetic product, with a lower impact on the user and on the environment.

A further significant advantage of the present composition lies on the fact that it proves to be fluid and easily applicable since the particles of graphene are oriented during the application, thus favoring the running and the definition of the eyelashes.

The use of the composition of the present invention as a mascara for eyelashes allows to obtain, in an optimal manner, the effects requested by clients: to increase the volume and the length of the eyelashes with an effect free from smudging and clumps, with a good separation between the eyelashes and an optimal curling of the eyelashes. The lengthening and volumizing effect has proved to be equal or superior to that obtained by mascaras containing polymers and synthetic fibers. Particularly, as shown in the examples, a composition according to the invention comprising graphene improves separation, length, thickness, resistance to expand.

If applied on the eyebrows, the present composition confers a volumizing and thickening effect capable of dying the eyebrows, thanks to the presence of pigments in the mascara of the invention, yet without painting or staining the skin.

According to a further embodiment, the present composition can be used as an eyeliner, showing optimal application features, that is, an easy distribution of the product, keeping at the same time a high definition.

Further, there is no release of color in contact with water over time ("long-lasting" effect), thus ensuring the long endurance of the eyeliner on the skin without the use of fixing agents that, in most of the products in commerce, are constituted by synthetic polymers.

This feature, particularly, is due to the specific presence of graphene that, by exercising a weakly hydrophobic effect (water contact angle of about) 87°, favors the improved endurance of the product on the skin, thus avoiding the formation of smudges of the product in the presence of water or humidity for a long time.

Such an effect is advantageously found also in the mentioned mascaras.

EXPERIMENTAL EXAMPLES

In the non-limiting examples shown below the compositions are shown according to the invention, except where differently indicated. Further, it is also shown the effect obtained for the application on standard artificial eyelashes and on eyebrows.

All the compositions in accordance with the invention have shown evident abilities to lengthen and volumize the eyelashes, to define, dye and thicken the eyebrows, to endure, and to define the eye contour. The quantities illustrated in the examples are expressed in grams; all these amounts can be freely modified within a weight range of ±10% of that amount: for example an amount of 3 grams can be also used in an interval comprised between 2.70 to 3.30 grams, etc.: accordingly, variants of the examples 1, 1B, 2, 2B, 3, 3B in which each of the given ingredients may vary within a weight range of ±10% its amount, are part of the present invention.

According to example 1, the emulsifier is represented by a mixture of starches (octenylsuccinate starch, tapioca starch, *Zea mays* starch), *Cyamopsis tetragonoloba* gum and *Citrus aurantium sinensis* fiber. The mixture of waxes is constituted by beeswax and carnauba wax. Consistency factors are glycerylmonostearate and glyceryl behenate. Vegetal oils are castor oil, isoamyl laureate and triglycerides of caprylic/capric acid. The white pigment is titanium dioxide, plus colored pigments. Tocopherol, benzyl alcohol and ethylhexylglycerin constitute the preserving and antioxidant system.

According to Example 3, the gelling agent is a mixture of Carboxymethylcellulose, Carrageenans, carrubo gum (*Ceratonia siliqua*), sucrose. The lenitives are constituted by Aloe Barbadensis leaf juice and *Chamomilla recutita* flower water. The emulsifier is glyceryl oleate citrate; the white pigment is titanium dioxide. Glycerin carries out the function of moistener, sodium hyaluronate is a moisturizer. Tocopherol, benzyl alcohol and ethylhexylglycerin constitute the preserving and antioxidant system.

The composition contains 10% of graphene by weight on the total weight of the composition.

Examples 1, 1A (reference) and 1B refer to compositions for mascara to be applied on eyelashes; examples 2 and 2B refer to compositions for mascara to be applied on eyebrows; examples 3 and 3B refer to compositions of eyeliner.

The reference compositions do not contain graphene.

EXAMPLE 1

| | |
|---|---|
| Zea Mays Starch, Sodium Starch Octenylsuccinate, Tapioca Starch, Cyamopsis Tetragonoloba Gum, Citrus Aurantium Sinensis Fiber | 3 |
| Glycerin | 4 |
| Glyceryl Stearate | 1.5 |
| Cera Alba Beeswax | 6 |
| Copernicia Cerifera (Carnauba) Wax | 3 |
| Caprylic/Capric Triglycerides | 6.5 |
| Aqua | q.b a 100 |
| Isoamyl laurate | 2.5 |
| Ricinus communis seed oil | 3 |
| Titanium dioxide | 0.5 |
| Graphene (Paste G+) | 10 |
| Benzyl Alcohol, Ethylhexylglycerin, Tocopherol | 1 |
| Tocopherol | 1 |
| Glyceryl behenate | 3 |
| Vegetal fibers | 7 |

EXAMPLE 1A

| | |
|---|---|
| Zea Mays Starch, Sodium Starch Octenylsuccinate, Tapioca Starch, Cyamopsis Tetragonoloba Gum, Citrus Aurantium Sinensis Fiber | 3 |
| Glyceryl Stearate | 1.5 |
| Cera Alba | 6 |
| Copernicia Cerifera (Carnauba) Wax | 3 |
| Caprylic/Capric Triglycerides | 6.5 |
| Ricinus communis seed oil | 3 |
| Isoamyl laurate | 2.5 |
| Titanium dioxide | 0.5 |
| Glycerin | 4 |
| Aqua | q.b a 100 |
| Vegetal fibers | 7 |
| C.I. 77266, Ceteareth-25, Sodium Carbonate, Sorbitol, Citric Acid | 5 |
| Benzyl Alcohol, Ethylhexylglycerin, Tocopherol | 1 |
| Tocopherol | 1 |
| Glyceryl behenate | 3 |

EXAMPLE 1B

| | |
|---|---|
| Zea Mays Starch, Sodium Starch Octenylsuccinate, Tapioca Starch, Cyamopsis Tetragonoloba Gum, Citrus Aurantium Sinensis Fiber | 3 |
| Glycerin | 4 |
| Glyceryl Stearate | 1.5 |
| Cera Alba Beeswax | 6 |
| Copernicia Cerifera (Carnauba) Wax | 3 |
| Caprylic/Capric Triglycerides | 6.5 |
| Aqua | q.b a 100 |
| Isoamyl laurate | 2.5 |
| Ricinus communis seed oil | 3 |
| Titanium dioxide | 0.5 |
| C.I. 77266, Ceteareth-25, Sodium Carbonate, Sorbitol, Citric Acid | 2.5 |
| Graphene (Paste G+) | 10 |
| Benzyl Alcohol, Ethylhexylglycerin, Tocopherol | 1 |
| Tocopherol | 1 |
| Glyceryl behenate | 3 |
| Vegetal fibers | 7 |

Commercial Mascara for Eyelashes (Reference)

INGREDIENTS: Aqua, Paraffin, Carnauba wax, Cera alba beeswax, Triethanolamine, Acacia senegal, Propylene glycol, Palmitic acid, Stearic acid, Glyceryl stearate, Peg-75 stearate, Hydrogenated polycyclopentadiene, Glycerin, Silica, Acrylates copolymer, Hydroxyethylcellulose, Sodium polymethacrylate, Ricinus communis oil, Sodium dehydroacetate, Tetrasodium disuccinoyl cystine, Methylparaben, Polyethylene, Imidazolidinyl urea, Cellulose, Pvp, Phenoxyethanol, Tocopherol, CI 77499, CI 77266.

EXAMPLE 2

| | |
|---|---|
| Potassium Cetyl Phosphate | 1.5 |
| Cellulose Gum, Carrageenan, Ceratonia Siliqua Gum, Sucrose | 1 |
| Glyceryl Stearate | 1.5 |
| Copernicia Cerifera (Carnauba) Wax | 3 |
| Cera Alba Beeswax | 6 |
| Caprylic/Capric Triglycerides | 3 |
| Ricinus communis seed oil | 0.5 |
| Isoamyl laurate | 3.5 |
| Titanium dioxide | 0.5 |
| Glycerin | 4 |
| Aqua | q.b a 100 |
| Vegetal fibers | 7 |
| Graphene (Paste G+) | 10 |
| Benzyl Alcohol, Ethylhexylglycerin, Tocopherol | 1 |
| Tocopherol | 1 |
| Glyceryl behenate | 3 |
| Mica | 3 |

EXAMPLE 2B

| | |
|---|---|
| Potassium Cetyl Phosphate | 1.5 |
| Cellulose Gum, Carrageenan, Ceratonia Siliqua Gum, Sucrose | 1 |
| Glyceryl Stearate | 1.5 |
| Copernicia Cerifera (Carnauba) Wax | 3 |
| Cera Alba Beeswax | 6 |
| Caprylic/Capric Triglycerides | 3 |
| Ricinus communis seed oil | 0.5 |
| Isoamyl laurate | 3.5 |
| Titanium dioxide | 0.5 |
| Glycerin | 4 |
| Aqua | q.b a 100 |
| Vegetal fibers | 7 |
| Graphene (Paste G+) | 10 |
| Benzyl Alcohol, Ethylhexylglycerin, Tocopherol | 1 |
| Tocopherol | 1 |
| Glyceryl behenate | 3 |
| Mica | 3 |
| C.I. 77266, Ceteareth-25, Sodium Carbonate, Sorbitol, Citric Acid | 2.5 |

Commercial Mascara for Eyebrows (Reference)

INGREDIENTS: Aqua/water/eau, peg/ppg-8/3 laurate, polyethylene, sodium polyacrylate, mica, paraffin, phenoxyethanol, ammonium acrylates copolymer, hydrolyzed wheat protein/pvp crosspolymer, isopropyl titanium triisostearate, denat, alcohol, lauric acid, argania spinosa kernel oil, ethylhexylglycerin, disodium deceth-6 sulfosuccinate, panthenol, laureth-30, sodium dehydroacetate, glycerin, potassium sorbate, biotin, disodium edta, hydrolyzed keratin, pantolactone, tocopherol, methylparaben, sodium sulfate, ethylparaben, butylparaben, propylparaben, Bambusa arundinacea leaf extract, sodium benzoate.

EXAMPLE 3

| | |
|---|---|
| Cellulose Gum, Carrageenan, Ceratonia Siliqua Gum, Sucrose | 0.8 |
| Aloe Barbadensis Leaf Juice | 20 |
| Chamomilla Recutita Flower Water | 20 |
| Glyceryl Oleate Citrate | 2.5 |
| Titanium dioxide | 0.5 |
| Glycerin | 3 |
| Aqua | q.b a 100 |

-continued

EXAMPLE 3

| Sodium Hyaluronate | 0.5 |
|---|---|
| Graphene (Paste G+) | 10 |
| Benzyl Alcohol, Ethylhexylglycerin, Tocopherol | 1 |

EXAMPLE 3B

| Cellulose Gum, Carrageenan, *Ceratonia Siliqua* Gum, Sucrose | 0.8 |
|---|---|
| *Aloe Barbadensis* Leaf Juice | 20 |
| *Chamomilla Recutita* Flower Water | 20 |
| Glyceryl Oleate Citrate | 2.5 |
| Titanium dioxide | 0.5 |
| Glycerin | 3 |
| Aqua | q.b a 100 |
| Sodium Hyaluronate | 0.5 |
| C.I. 77266, Ceteareth-25, Sodium Carbonate, Sorbitol, Citric Acid | 2.5 |
| Benzyl Alcohol, Ethylhexylglycerin, Tocopherol | 1 |
| Graphene (Paste G+) | 10 |

Commercial Eye-Liner (Reference)

INGREDIENTS: Aqua, polysorbate 20, polysorbate 80, sorbitan stearate, glycerin, mica, sorbitol, talc, magnesium aluminum silicate, phenoxyethanol, hydroxypropyl methylcellulose, propylene glycol, *Tilia cordata* flower extract, *Helianthus annuus* seed oil, disodium edta, *Chamomilla recutita* flower extract, tocopherol, sodium dehydroacetate, imidazolidinyl urea, bha, potassium sorbate, CI 77499, CI 77891.

Figure 2:
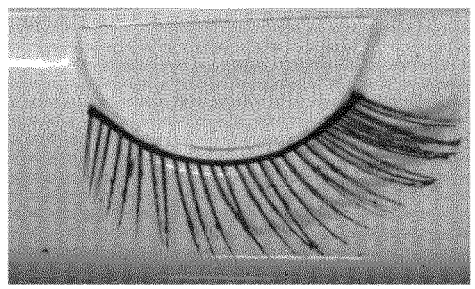
FIGS. 2A-D: covering effect on artificial eyelashes obtained by the compositions according to: (A) example 1; (B) reference example 1A; (C) example 1B; (D) commercial reference.
Figure 2:
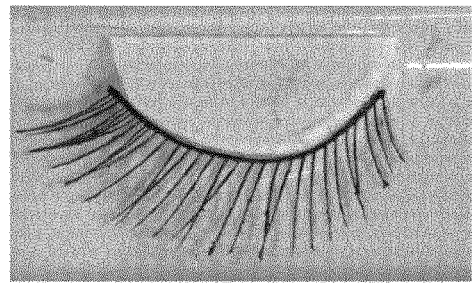
Figure 2:
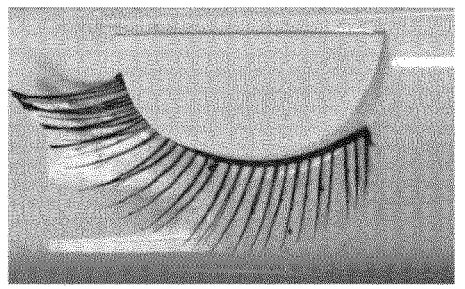
Figure 2:
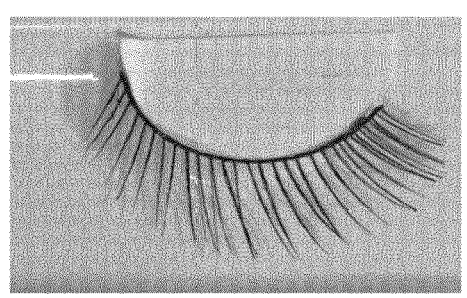

As shown in FIGS. 2A and 2C, the mascara prepared according to examples 1 and 1B has proved to be easily applicable on fake eyelashes and presents the following effects: volumized, curled, thickened and longer eyelashes, free from clumps, not expanded even in the presence of humidity.

FIG. 2D shows the result of the use of a commercial mascara as defined above that has been applied on fake eyelashes, determining a less volumizing and thickening effect compared to that obtained with the composition of the present invention applied on fake eyelashes (FIGS. 2A and 2C).

FIG. 2B shows the result of the application of the composition according to example 1A, wherein graphene was not present, which has been more difficult to distribute evenly on the eyelashes, thus forming small clumps and irregular thickenings on the eyelashes.

Figure 3:
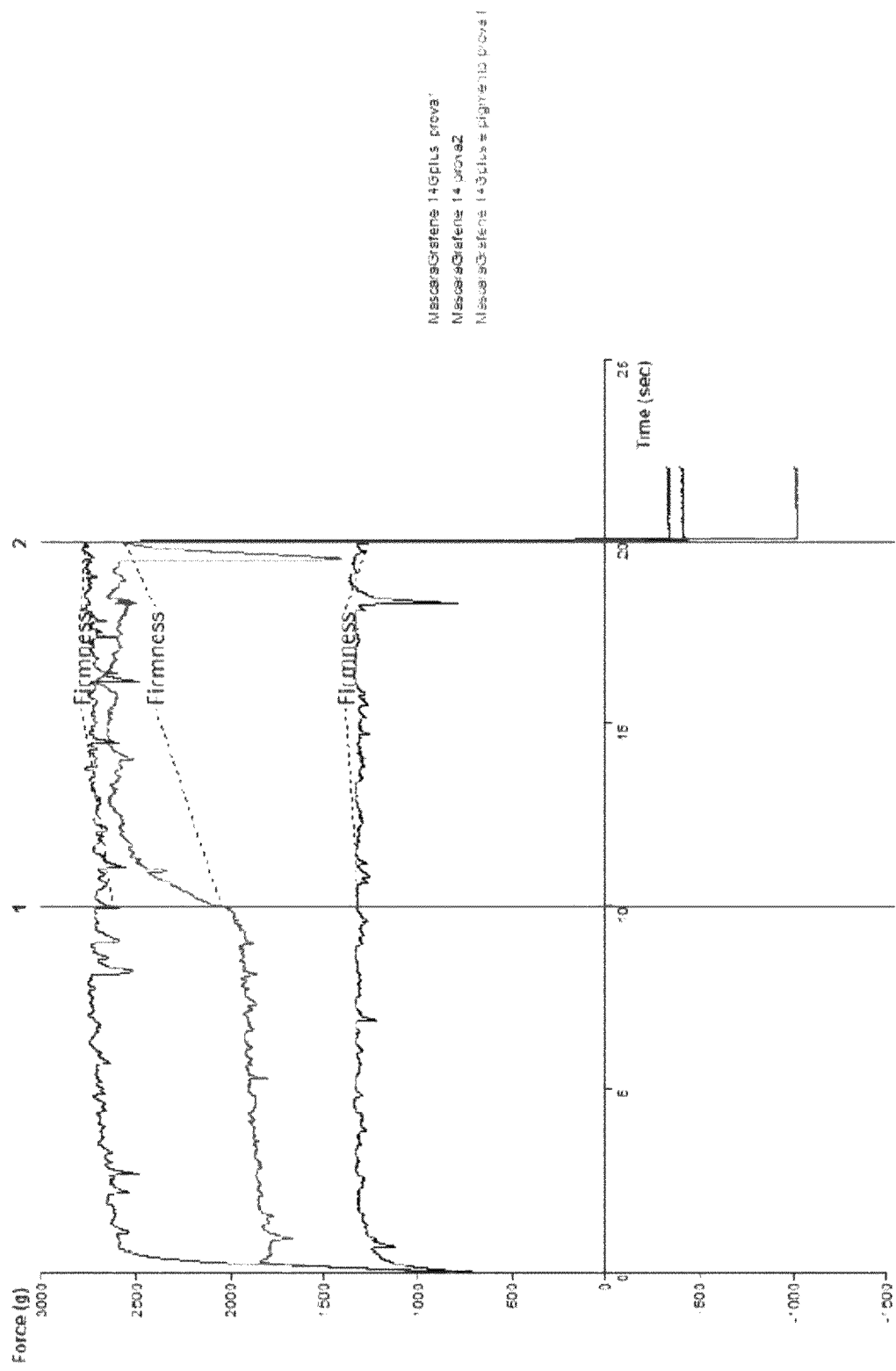
FIG. 3: compactness analysis ("firmness") of the composition according to examples 1, 1A and 1B.

FIG. 3 shows a texture analysis of the mascaras obtained according to the compositions defined in examples 1, 1A and 1B. As can be seen from the graph, the composition containing only graphene (according to example 1) shows the highest compactness (firmness) with respect to the other two compositions. The composition that shows the lowest compactness is the one according to example 1A, which does not contain graphene.

Figure 4:
FIG. 4: covering effect on eyebrows obtained by the composition of the invention according to example 2 (volunteer's left eye) in comparison with commercial reference (right eye).

FIG. 4 indicates an effect on the eyebrows that is more evident and with a better definition due to the application of the product relative to the present invention containing graphene, compared to the commercial product.

The invention claimed is:

1. A natural-based make-up cosmetic composition comprising graphene, said composition being free from synthetic polymers, wherein said graphene is present in a weight percentage between 5% and 15% on the weight of the composition and is in the form of particles having a length between 5 and 10 µm and a thickness between 0.5 and 5 nm; and wherein the composition is a mascara or an eyeliner.

2. The composition according to claim 1, wherein said composition is an eyeliner.

3. The composition according to claim 2, wherein said graphene is present in a weight percentage of 10% on the weight of the composition.

4. The composition according to claim 1, comprising waxes in a weight percentage between 2 and 20% on the weight of the composition, said composition being a mascara.

5. The composition according to claim 1, further comprising 1-10% emulsifiers, 2-20% oils, and 0.5-20% dyes.

6. The composition according to claim 1, wherein said oils comprise, in weight on the weight of the composition, 1.5-3.5% castor oil and 2.0-3.0% isoamyl laurate, said mascara being applicable on eyelashes.

7. The composition according to claim 1, wherein said oils comprise, in weight on the weight of the composition, 0.3-0.7% castor oil and 3.0-4.0% isoamyl laurate, said mascara being applicable on eyebrows.

8. The composition according to claim 7, further comprising, in weight on the weight of the composition, 2.5-3.5% mica.

9. The composition according to claim 2, comprising waxes in a weight percentage between 2 and 20% on the weight of the composition, said composition being a mascara.

10. The composition according to claim 3, comprising waxes in a weight percentage between 2 and 20% on the weight of the composition, said composition being a mascara.

11. The composition according to claim 2, further comprising 1-10% emulsifiers, 2-20% oils, and 0.5-20% dyes.

12. The composition according to claim 3, further comprising 1-10% emulsifiers, 2-20% oils, and 0.5-20% dyes.

13. The composition according to claim 4, further comprising 1-10% emulsifiers, 2-20% oils, and 0.5-20% dyes.

14. The composition according to claim 2, wherein said oils comprise, in weight on the weight of the composition, 1.5-3.5% castor oil and 2.0-3.0% isoamyl laurate, said mascara being applicable on eyelashes.

15. The composition according to claim 3, wherein said oils comprise, in weight on the weight of the composition, 1.5-3.5% castor oil and 2.0-3.0% isoamyl laurate, said mascara being applicable on eyelashes.

* * * * *